(12) United States Patent
Ito et al.

(10) Patent No.: US 10,322,437 B2
(45) Date of Patent: Jun. 18, 2019

(54) STACKED ULTRASOUND VIBRATION DEVICE AND ULTRASOUND MEDICAL APPARATUS

(71) Applicant: OLYMPUS CORPORATION, Tokyo (JP)

(72) Inventors: Hiroshi Ito, Koganei (JP); Koichi Shiotani, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 432 days.

(21) Appl. No.: 15/221,087

(22) Filed: Jul. 27, 2016

(65) Prior Publication Data

US 2016/0332197 A1 Nov. 17, 2016

Related U.S. Application Data

(63) Continuation of application No. PCT/JP2015/051542, filed on Jan. 21, 2015.

(30) Foreign Application Priority Data

Jan. 27, 2014 (JP) .................................. 2014-012687

(51) Int. Cl.
*H01L 41/083* (2006.01)
*H01L 41/047* (2006.01)
(Continued)

(52) U.S. Cl.
CPC .... *B06B 1/0611* (2013.01); *A61B 17/320068* (2013.01); *B06B 3/00* (2013.01);
(Continued)

(58) Field of Classification Search
CPC ..... B06B 1/0611; B06B 3/00; H01L 41/0471; H01L 41/277; H01L 24/29; H01L 41/32;
(Continued)

(56) References Cited

U.S. PATENT DOCUMENTS

| 4,582,240 | A | 4/1986 | Lux et al. |
| 6,291,930 | B1 | 9/2001 | Sager |
| 2004/0113215 | A1 | 7/2004 | Shimada et al. |
| 2009/0295256 | A1 | 12/2009 | Okamura et al. |
| 2010/0058875 | A1* | 3/2010 | Baumgartner .......... G01L 9/008 73/723 |

(Continued)

FOREIGN PATENT DOCUMENTS

| EP | 1 898 476 A1 | 3/2008 |
| EP | 2 800 400 A1 | 11/2014 |

(Continued)

OTHER PUBLICATIONS

International Search Report dated Mar. 17, 2015 issued in PCT/JP2015/051542.

(Continued)

*Primary Examiner* — Thomas M Dougherty
(74) *Attorney, Agent, or Firm* — Scully, Scott, Murphy & Presser, P.C.

(57) ABSTRACT

A stacked ultrasound vibration device is provided with a plurality of piezoelectric bodies between two mass materials, in which brazing materials with an elastic constant smaller than elastic constants of the two mass materials and the plurality of piezoelectric bodies are used to bond the plurality of piezoelectric bodies as similar material bonding portions by a first metal bonding layer with a first thickness and to bond the plurality of piezoelectric bodies and the mass materials as dissimilar material bonding portions by a second metal bonding layer with a second thickness thicker than the first thickness.

10 Claims, 10 Drawing Sheets

(51) Int. Cl.
*H01L 41/09* (2006.01)
*B06B 1/06* (2006.01)
*H01L 41/277* (2013.01)
*B06B 3/00* (2006.01)
*A61B 17/32* (2006.01)
*H01L 23/00* (2006.01)
*A61B 18/00* (2006.01)
*A61N 7/00* (2006.01)

(52) U.S. Cl.
CPC ........ *H01L 41/0471* (2013.01); *H01L 41/277* (2013.01); *A61B 2018/00607* (2013.01); *A61N 2007/0078* (2013.01); *H01L 24/29* (2013.01); *H01L 24/32* (2013.01); *H01L 24/50* (2013.01); *H01L 24/86* (2013.01); *H01L 2224/29111* (2013.01); *H01L 2224/32145* (2013.01)

(58) Field of Classification Search
CPC ................ H01L 24/50; H01L 24/86; H01L 2224/29111; H01L 2224/32145; A61N 2007/0078; A61B 17/320068; A61B 2917/00607
USPC .......................................................... 310/366
See application file for complete search history.

(56) References Cited

U.S. PATENT DOCUMENTS

| | | |
|---|---|---|
| 2013/0161421 A1 | 6/2013 | Okamura et al. |
| 2013/0168465 A1 | 7/2013 | Okamura et al. |
| 2014/0309562 A1 | 10/2014 | Ito |
| 2015/0145379 A1* | 5/2015 | Ito .................. A61B 17/320092 310/363 |
| 2018/0159503 A1* | 6/2018 | Takano ................ B23K 1/0016 |

FOREIGN PATENT DOCUMENTS

| | | |
|---|---|---|
| EP | 2 881 183 A1 | 6/2015 |
| JP | 3-174782 A | 7/1991 |
| JP | 4-343282 A | 11/1992 |
| JP | 2007-43094 A | 2/2007 |
| JP | 2008-128875 A | 6/2008 |
| JP | 2013-135301 A | 7/2013 |
| WO | WO 2006/135013 A1 | 12/2006 |
| WO | WO 2013/099482 A1 | 7/2013 |

OTHER PUBLICATIONS

Extended Supplementary European Search Report dated Sep. 18, 2017 in European Patent Application No. 15 73 9798.5.

* cited by examiner

STACKED ULTRASOUND VIBRATION DEVICE AND ULTRASOUND MEDICAL APPARATUS

CROSS REFERENCE TO RELATED APPLICATION

This application is a continuation application of PCT/JP2015/051542 filed on Jan. 21, 2015 and claims benefit of Japanese Application No. 2014-012687 filed in Japan on Jan. 27, 2014, the entire contents of which are incorporated herein by this reference.

BACKGROUND OF THE INVENTION

1. Field of the Invention

The present invention relates to a stacked ultrasound vibration device configured to excite ultrasound vibration and an ultrasound medical apparatus including the stacked ultrasound vibration device.

2. Description of the Related Art

Among ultrasound treatment instruments configured to utilize ultrasound vibration to perform a coagulation/dissection treatment of living tissue, there is an ultrasound treatment instrument including an ultrasound vibrator using a piezoelectric transducer as an ultrasound vibration source in a handpiece.

Among the ultrasound vibrators, there is an ultrasound vibrator including piezoelectric elements configured to convert an electrical signal to mechanical vibration, and the piezoelectric elements are sandwiched between two block-shaped metal members serving as a front mass or a back mass. The piezoelectric elements and the metal members are integrated by some kind of method such as adhesion, and they integrally vibrate. Such an ultrasound transducer is called a Langevin transducer.

An example of a known method of integrating the piezoelectric elements and the metal members in the Langevin transducer includes a bolt clamped Langevin transducer in which piezoelectric elements are placed between two metal members. In the bolt clamped Langevin transducer, the piezoelectric elements and the metal members are firmly fastened by a bolt, and the entire piezoelectric elements and metal members integrally vibrate.

In general, lead zirconate titanate (PZT, $Pb(Zr_x, Ti_{1-x})O3$) is used for the piezoelectric elements used in the bolt clamped Langevin transducer. A shape of the piezoelectric elements is processed into a ring shape, and the bolt is pushed and inserted into the inside.

Productivity and electromechanical conversion efficiency of PZT are high, and PZT has good characteristics as a piezoelectric material. Therefore, PZT is used in various fields of ultrasound transducers, actuators, and the like for a long time.

However, lead is used in PZT, and use of a non-lead piezoelectric material without using lead has been desired in recent years from the viewpoint of preventing adverse effects on the environment. An example of a known non-lead piezoelectric material with high electromechanical conversion efficiency includes lithium niobate (LiNbO3) piezoelectric single crystals.

A method of placing piezoelectric elements between metal blocks and integrally bonding the piezoelectric elements and the metal blocks has been conventionally known as a configuration for inexpensively realizing a Langevin transducer using lithium niobate. Particularly, when a brazing material such as a solder is used to bond the metal blocks and the piezoelectric elements without using an adhesive, the Langevin transducer can obtain better vibration characteristics than those of the adhesive.

However, a high temperature process is generally necessary to bond the metal blocks and the piezoelectric elements by a brazing material such as a solder. There is a problem that the piezoelectric elements with piezoelectric single crystals crack due to thermal stress at dissimilar material bonding portions that are parts where the metal blocks and the piezoelectric elements are bonded.

An example of a disclosed technique for solving the problem includes an ultrasound vibrator of Japanese Patent Application Laid-Open Publication No. 2008-128875. A technique is known in the conventional ultrasound vibrator, in which structures, such as grooves and depressions, are provided on a bonding surface of each metal block bonded with an adhesive to electrodes provided on both upper and lower surfaces of a piezoelectric transducer. Therefore, generation of a shear strain during drive is suppressed, and a dielectric loss on the bonding surface is reduced. Furthermore, in the technique, generation of a crack in the piezoelectric transducer is prevented, and a vibration mode is stabilized.

SUMMARY OF THE INVENTION

An aspect of the present invention provides a stacked ultrasound vibration device comprising a plurality of piezoelectric bodies and mass material, wherein the plurality of piezoelectric bodies are bonded each other as similar material bonding portion by a first metal bonding layer with a first thickness, wherein the piezoelectric body and the mass material are bonded as dissimilar material bonding portion by a second metal bonding layer with a second thickness thicker than the first thickness, and wherein the first metal bonding layer and the second metal bonding layer comprise brazing material whose elastic constant is smaller than elastic constants of the plurality of piezoelectric bodies and the mass material.

An aspect of the present invention provides an ultrasound medical apparatus including: the stacked ultrasound vibration device comprising a plurality of piezoelectric bodies and mass material, wherein the plurality of piezoelectric bodies are bonded each other as similar material bonding portion by a first metal bonding layer with a first thickness, wherein the piezoelectric body and the mass material are bonded as dissimilar material bonding portion by a second metal bonding layer with a second thickness thicker than the first thickness, and wherein the first metal bonding layer and the second metal bonding layer comprise brazing material whose elastic constant is smaller than elastic constants of the plurality of piezoelectric bodies and the mass material; and a probe distal end portion configured to receive ultrasound vibration generated by the stacked ultrasound vibration device to treat living tissue.

DETAILED DESCRIPTION OF THE PREFERRED EMBODIMENT

Hereinafter, the present invention will be described with reference to the drawings. Note that in the following description, the drawings based on respective embodiments are schematic drawings, and a relationship between thickness and width of each part, a ratio of the thickness of respective parts, and the like are different from the reality. The relationship or the ratio of respective dimensions between the drawings may also be different in some parts of the drawings.

First, an embodiment of an ultrasound medical apparatus including a stacked ultrasound vibration device configured to excite ultrasound vibration according to an aspect of the present invention will be described with reference to the drawings.

Figure 1:
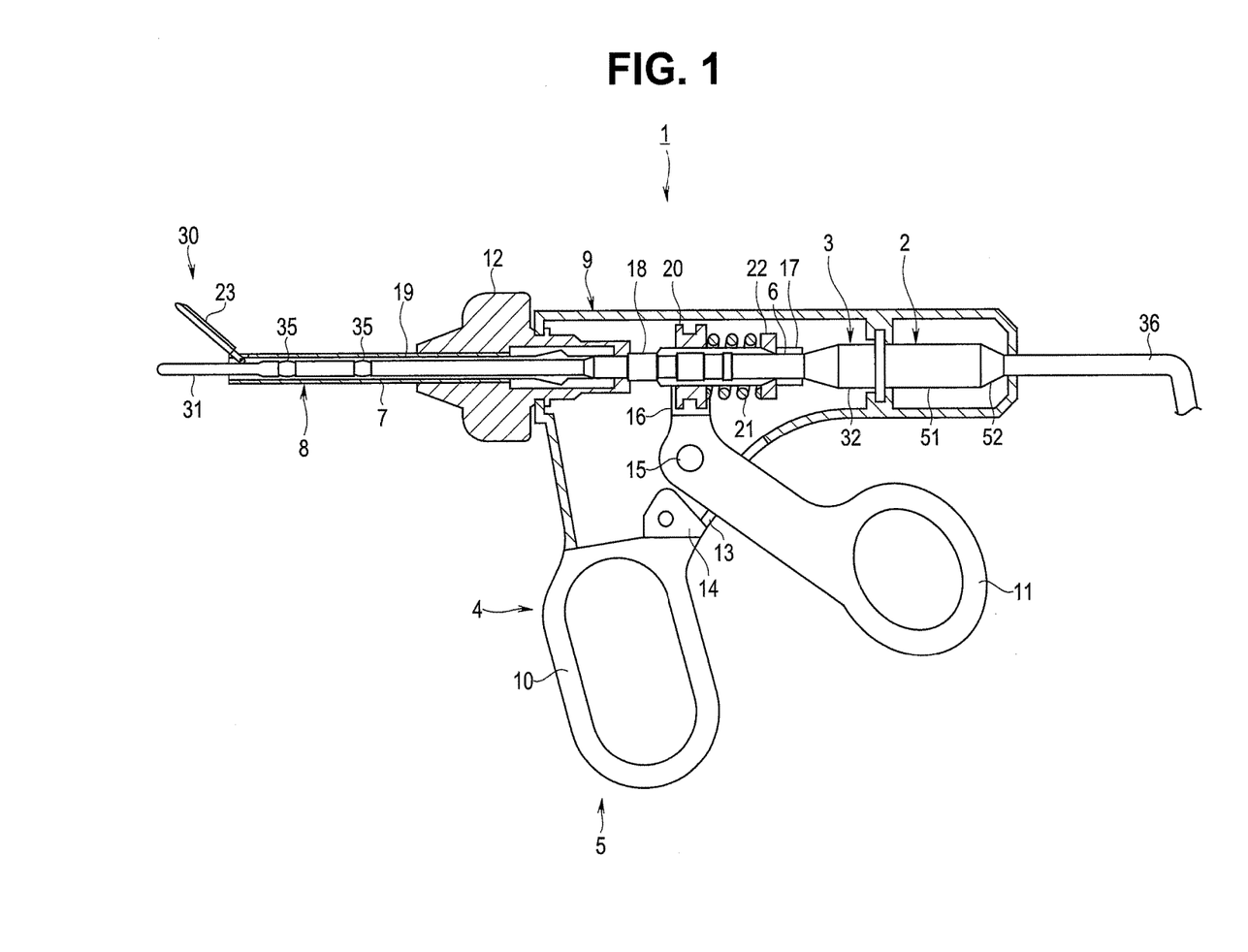
FIG. 1 is a cross-sectional view showing an entire configuration of an ultrasound medical apparatus according to an aspect of the present invention.
Figure 2:
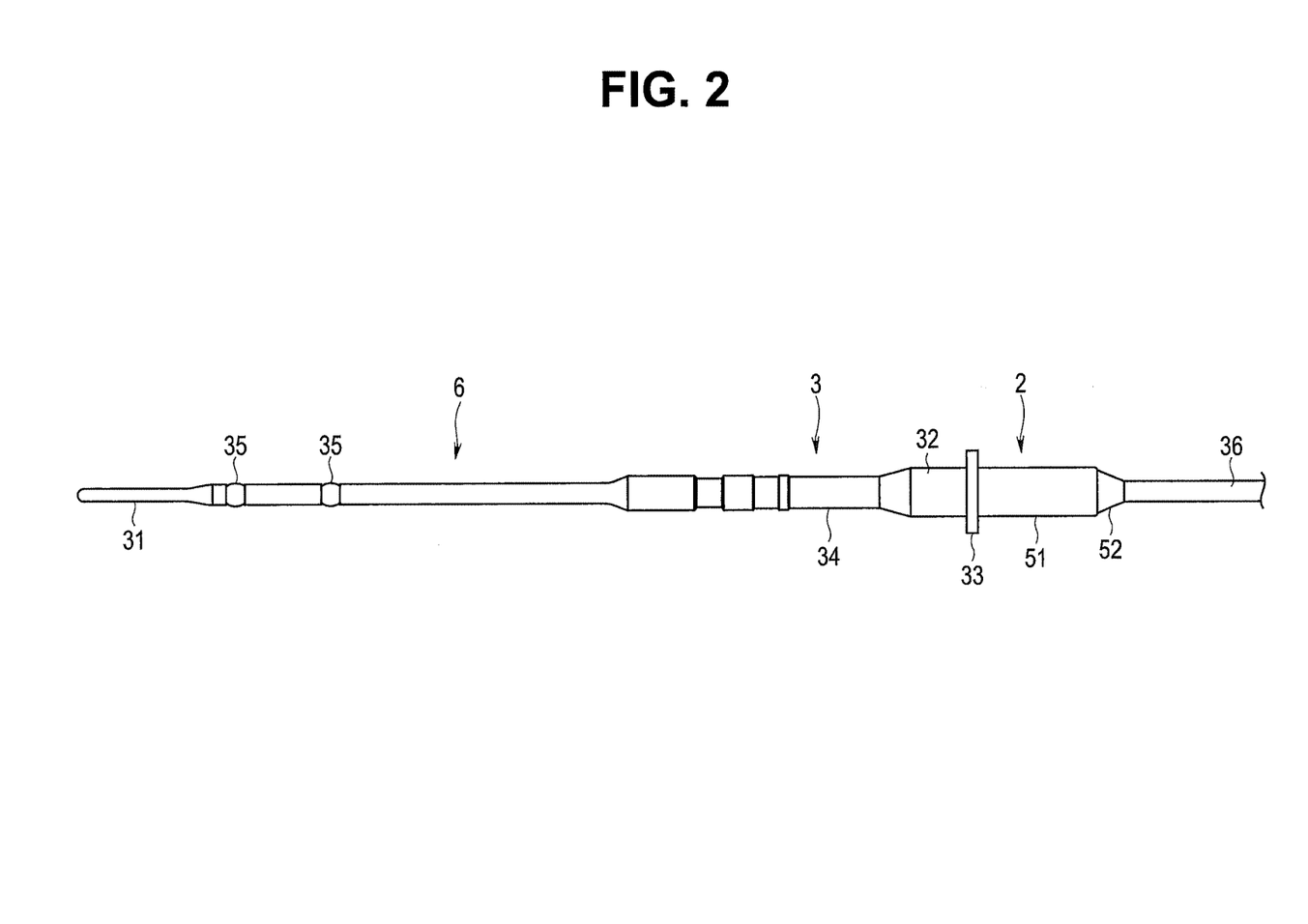
FIG. 2 is a diagram showing a schematic configuration of an entire transducer unit according to the aspect of the present invention.
Figure 3:
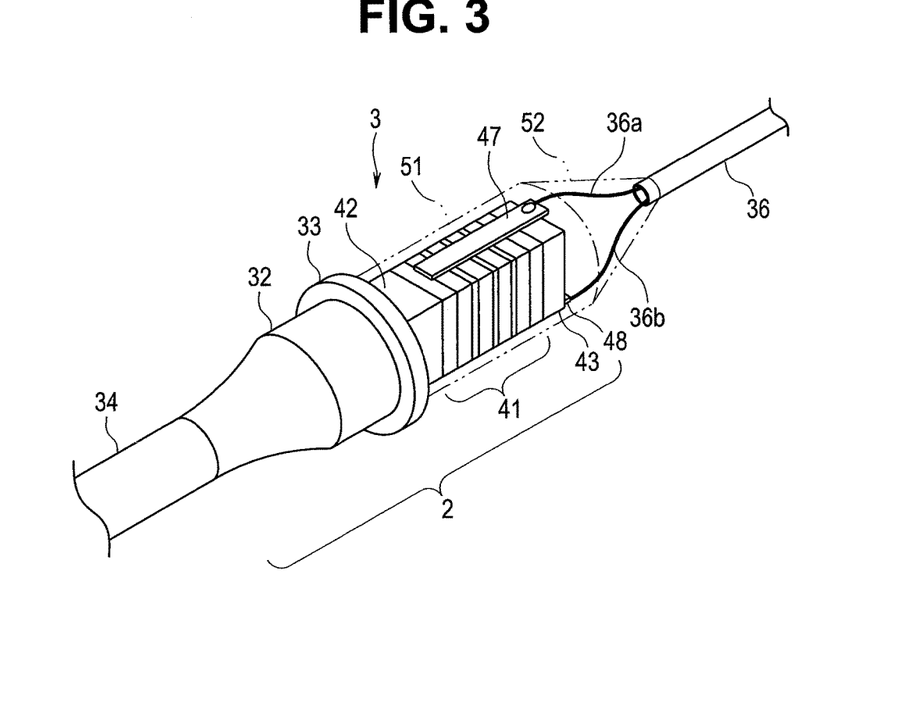
FIG. 3 is a perspective view showing a configuration of an ultrasound transducer according to the aspect of the present invention.
Figure 4:
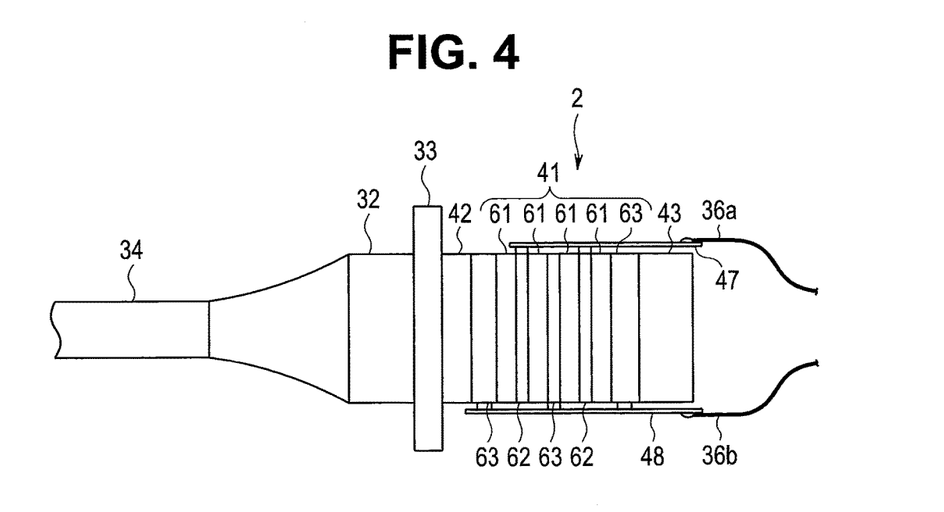
FIG. 4 is a side view showing the configuration of the ultrasound transducer according to the aspect of the present invention.
Figure 5:
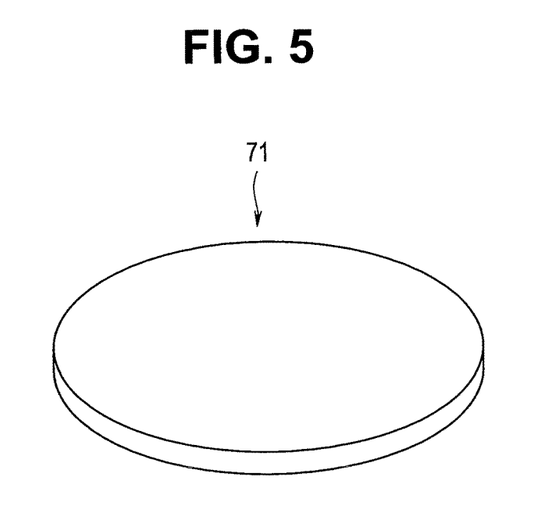
FIG. 5 is a perspective view showing a piezoelectric single crystal wafer according to the aspect of the present invention.
Figure 6:
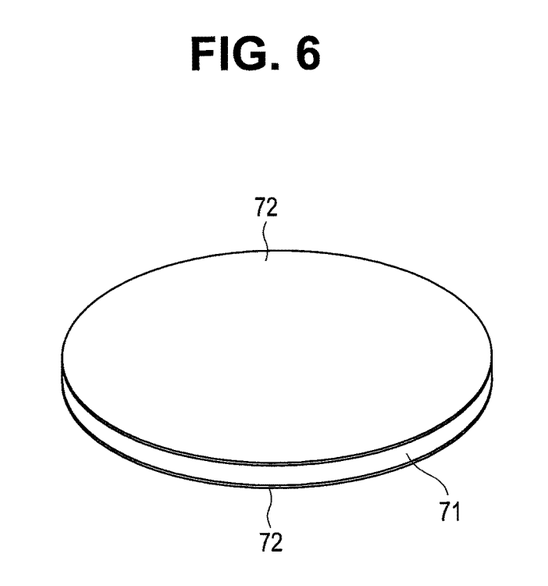
FIG. 6 is a perspective view showing the piezoelectric single crystal wafer provided with base metals according to the aspect of the present invention.
Figure 7:
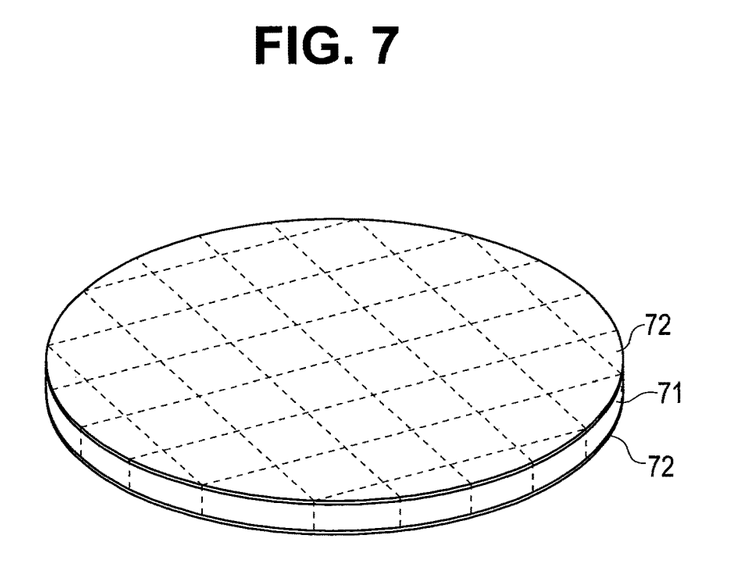
FIG. 7 is a perspective view showing the piezoelectric single crystal wafer to be diced according to the aspect of the present invention.
Figure 8:
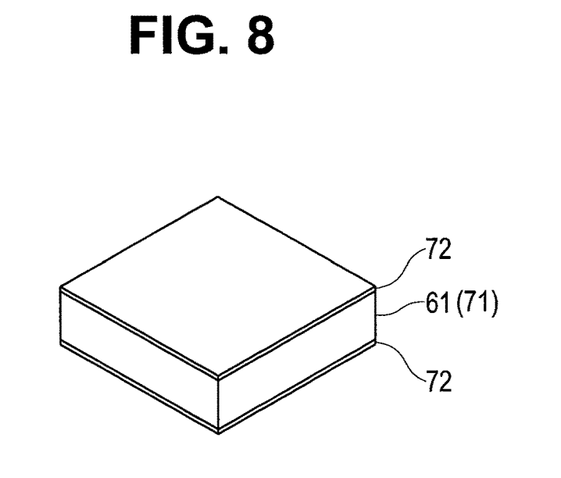
FIG. 8 is a perspective view showing piezoelectric single crystal bodies cut out from the piezoelectric single crystal wafer according to the aspect of the present invention.
Figure 9:
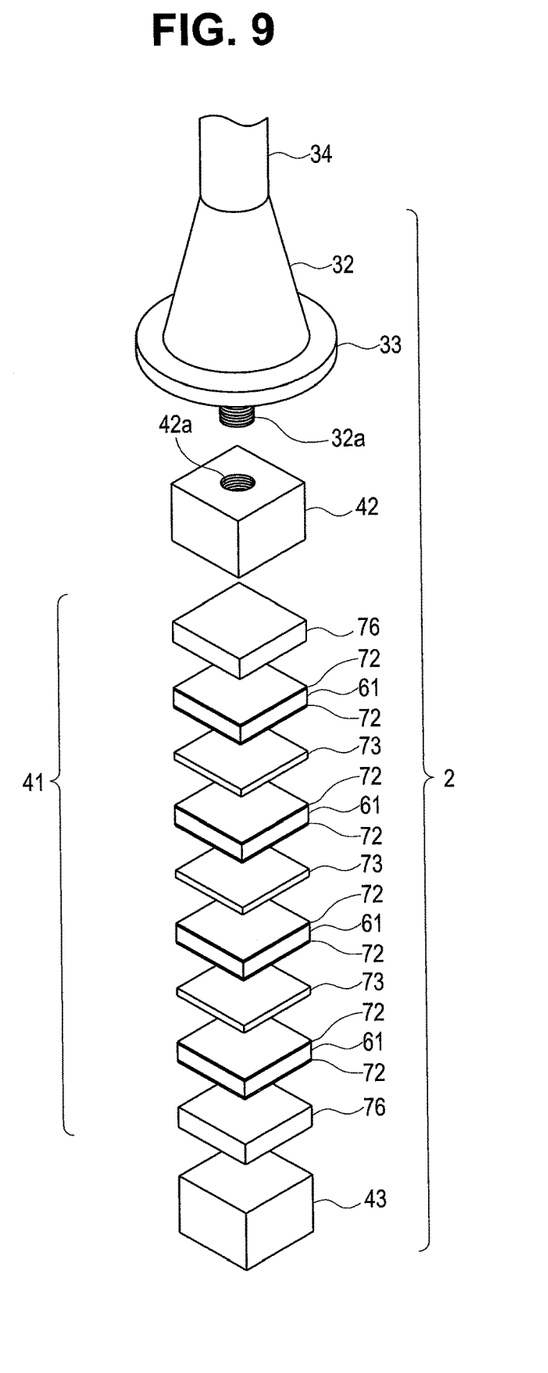
FIG. 9 is an exploded perspective view of the transducer unit including the ultrasound transducer according to the aspect of the present invention.
Figure 10:
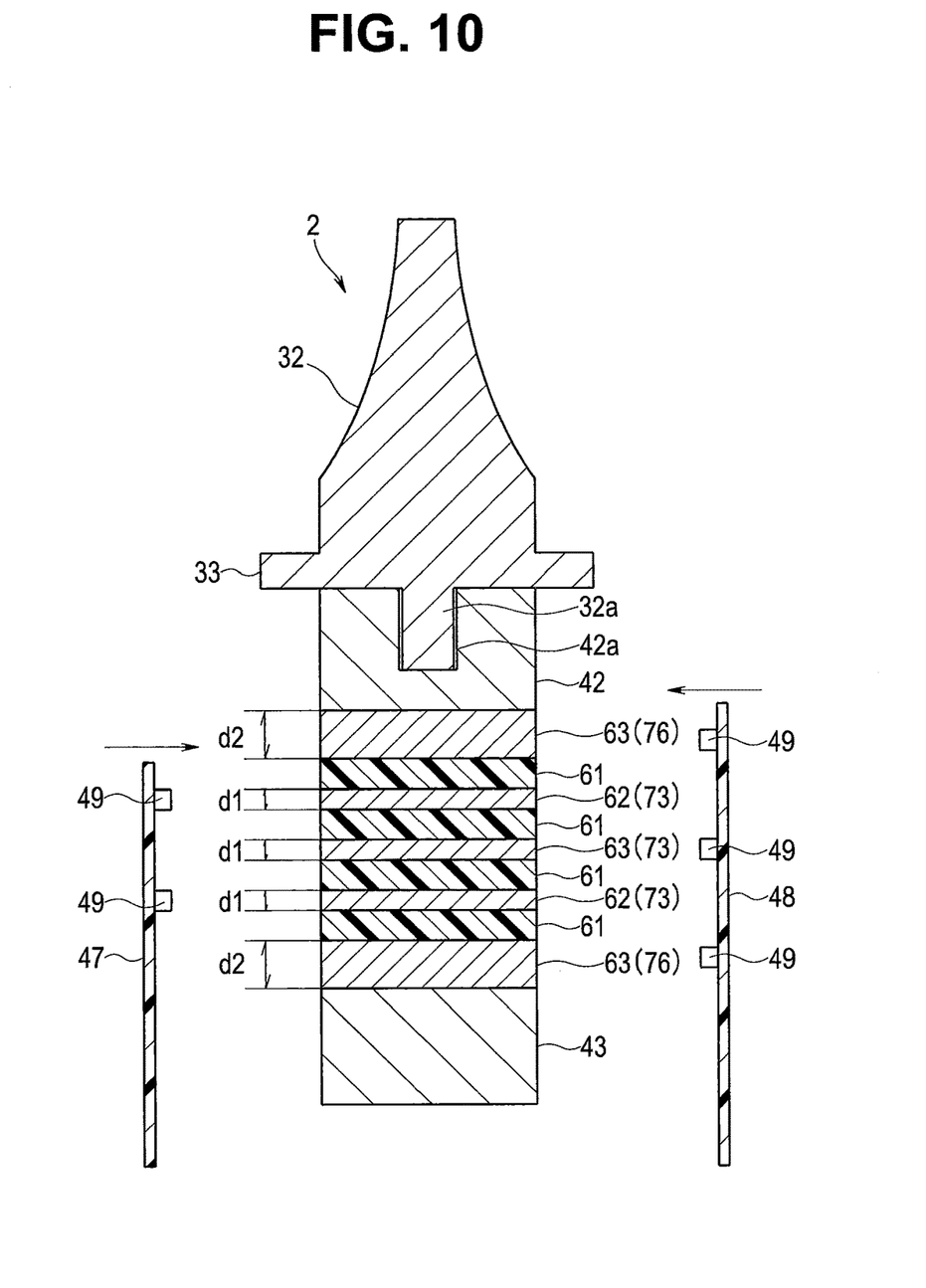
FIG. 10 is a cross-sectional view before flexible printed substrates are mounted on the ultrasound transducer of the transducer unit according to the aspect of the present invention.
Figure 11:
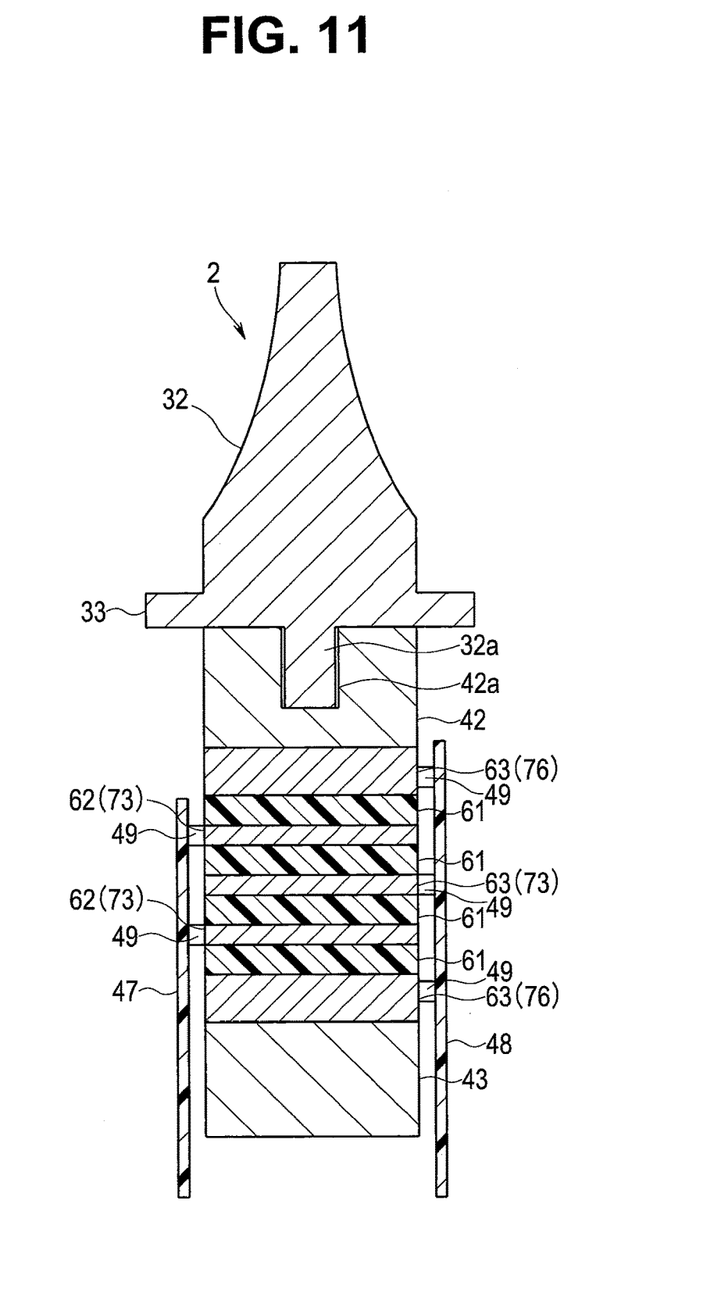
FIG. 11 is a cross-sectional view after the flexible printed substrates are mounted on the ultrasound transducer of the transducer unit according to the aspect of the present invention.
Figure 12:
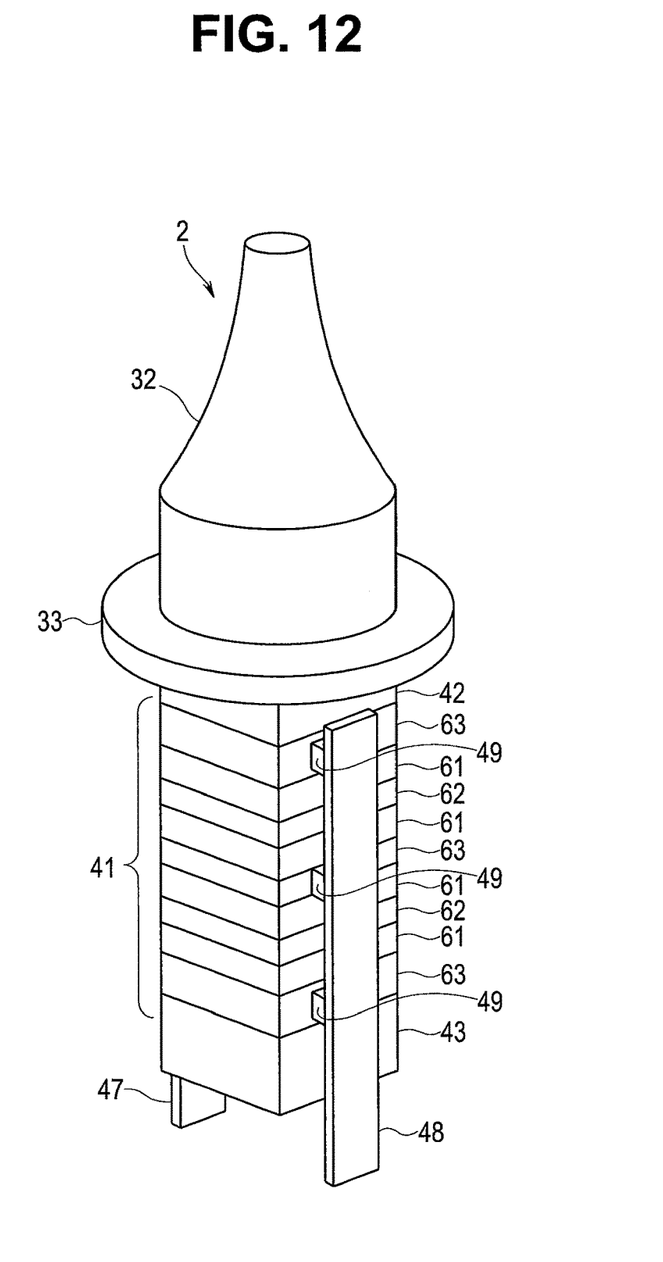
FIG. 12 is a perspective view showing the transducer unit in which the FPCs are mounted on the ultrasound transducer according to the aspect of the present invention.
Figure 13:
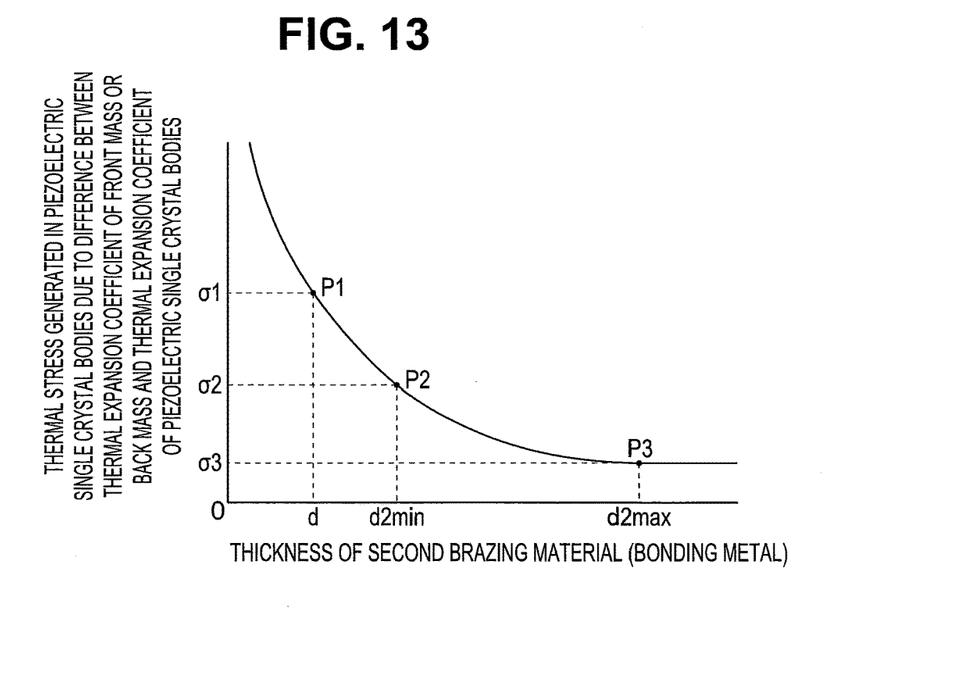
FIG. 13 is a graph showing a relationship between thickness of bonding metals and thermal stress generated in the piezoelectric single crystal bodies due to a difference between a thermal expansion coefficient of mass materials and a thermal expansion coefficient of the piezoelectric single crystal bodies according to the aspect of the present invention.
Figure 14:
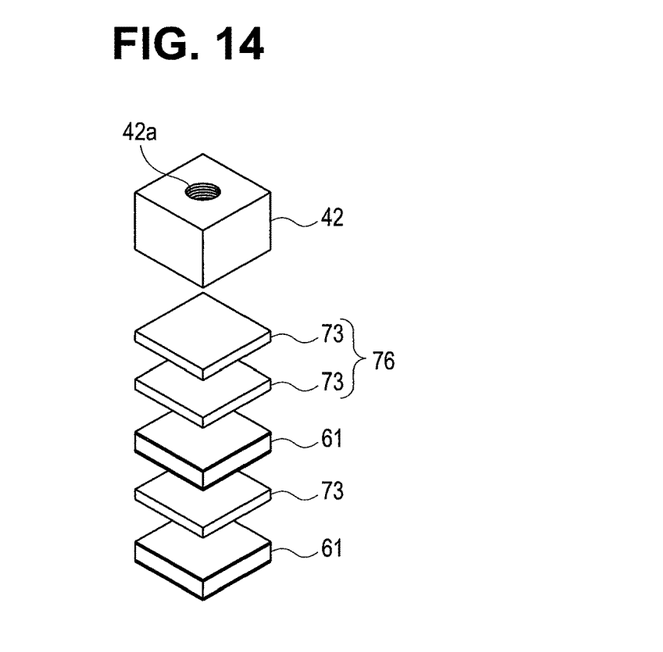
FIG. 14 is an exploded perspective view showing an example of the bonding metals provided between the mass materials and the piezoelectric single crystal bodies according to the aspect of the present invention.

FIG. 1 is a cross-sectional view showing an entire configuration of an ultrasound medical apparatus. FIG. 2 is a diagram showing a schematic configuration of an entire transducer unit. FIG. 3 is a perspective view showing a configuration of an ultrasound transducer. FIG. 4 is a side view showing the configuration of the ultrasound transducer. FIG. 5 is a perspective view showing a piezoelectric single crystal wafer. FIG. 6 is a perspective view showing the piezoelectric single crystal wafer provided with base metal. FIG. 7 is a perspective view showing the piezoelectric single crystal wafer to be diced. FIG. 8 is a perspective view showing piezoelectric single crystal bodies cut out from the piezoelectric single crystal wafer. FIG. 9 is an exploded perspective view of the transducer unit including the ultrasound transducer. FIG. 10 is a cross-sectional view before flexible printed substrates are mounted on the ultrasound transducer of the transducer unit. FIG. 11 is a cross-sectional view after the flexible printed substrates are mounted on the ultrasound transducer of the transducer unit. FIG. 12 is a perspective view showing the transducer unit in which the FPCs are mounted on the ultrasound transducer. FIG. 13 is a graph showing a relationship between thickness of bonding metals and thermal stress generated in the piezoelectric single crystal bodies due to a difference between a thermal expansion coefficient of mass materials and a thermal expansion coefficient of the piezoelectric single crystal bodies. FIG. 14 is an exploded perspective view showing an example of the bonding metals provided between the mass materials and the piezoelectric single crystal bodies.

(Ultrasound Medical Apparatus)

An ultrasound medical apparatus 1 shown in FIG. 1 is mainly provided with: a transducer unit 3 including an ultrasound transducer 2 configured to generate ultrasound vibration; and a handle 4 configured to use the ultrasound vibration to perform a coagulation/dissection treatment of a diseased part.

The handle 4 includes an operation portion 5, an insertion sheath 8 including a long mantle tube 7, and a distal end treatment portion 30. A proximal end portion of the insertion sheath 8 is attached to the operation portion 5 and is rotatable about an axial direction.

The distal end treatment portion 30 is provided on a distal end of the insertion sheath 8. The operation portion 5 of the handle 4 includes an operation portion main body 9, a fixed handle 10, a movable handle 11, and a rotation knob 12. The operation portion main body 9 is formed integrally with the fixed handle 10.

A slit 13 for inserting the movable handle 11 is formed on a back side a connection portion of the operation portion main body 9 and the fixed handle 10. An upper part of the movable handle 11 is extended inside the operation portion main body 9 through the slit 13.

A handle stopper 14 is fixed to an end portion of a lower side of the slit 13. The movable handle 11 is pivotably attached to the operation portion main body 9 through a handle support shaft 15. Along with an action of the movable handle 11 rotating about the handle support shaft 15, the movable handle 11 is configured to open and close relative to the fixed handle 10.

A substantially U-shaped connection arm 16 is provided on an upper end portion of the movable handle 11. The insertion sheath 8 includes: the mantle tube 7; and an operation pipe 17 inserted into the mantle tube 7 and movable in an axis direction.

A large diameter portion 18 with a diameter larger than a distal end side part is formed on a proximal end portion of the mantle tube 7. The rotation knob 12 is mounted around the large diameter portion 18.

A ring-shaped slider 20 is provided on a circumference surface of an operation pipe 19 and is movable in an axis direction. Behind the slider 20, a fixation ring 22 is disposed through a coil spring (elastic member) 21.

Furthermore, a proximal end portion of a grasper 23 is pivotably connected to a distal end portion of the operation pipe 19 through a working pin. The grasper 23 forms a treatment portion of the ultrasound medical apparatus 1 along with a distal end portion 31 of a probe 6. At an action of the operation pipe 19 moving in the axis direction, the grasper 23 is pushed and pulled in a front-back direction through the working pin.

In this case, at an action of the operation pipe 19 moved and operated toward a hand side, the grasper 23 is rotated counterclockwise about a fulcrum pin through the working pin.

As a result, the grasper 23 rotates in a direction approaching the distal end portion 31 of the probe 6 (closing direction). In this case, living tissue can be grasped between the single-swing grasper 23 and the distal end portion 31 of the probe 6.

In a state that the living tissue is grasped, power is supplied from an ultrasound power source to the ultrasound transducer 2 to vibrate the ultrasound transducer 2. The ultrasound vibration is transmitted to the distal end portion 31 of the probe 6. The ultrasound vibration is used to perform a coagulation/dissection treatment of the living tissue grasped between the grasper 23 and the distal end portion 31 of the probe 6.

(Transducer Unit)

Here, the transducer unit 3 will be described.

As shown in FIG. 2, the transducer unit 3 is assembled by integrating the ultrasound transducer 2 and the probe 6 that is a rod-shaped vibration transmission member configured to transmit the ultrasound vibration generated by the ultrasound transducer 2.

A horn 32 configured to amplify the vibration amplitude generated by the ultrasound transducer is consecutively connected to the ultrasound transducer 2. The horn 32 is made of stainless steel, duralumin, or a titanium alloy such as 64Ti (Ti-6Al-4V).

The horn 32 is formed in a conic shape with an external diameter decreasing toward the distal end side, and an outward flange 33 is disposed on a proximal end circumference portion. Note that the shape of the horn 32 here is not limited to the conic shape, and the shape may be an index shape with the external diameter exponentially decreasing toward the distal end side or a step shape with the external diameter decreasing toward the distal end side in stages.

The probe 6 includes a probe main body 34 made of a titanium alloy such as 64Ti (Ti-6Al-4V). The ultrasound transducer 2 consecutively connected to the horn 32 is disposed on a proximal end portion side of the probe main body 34.

In this way, the transducer unit 3 is formed by integrating the probe 6 and the ultrasound transducer 2. Note that the probe main body 34 and the horn 32 are screwed in the probe 6, and the probe main body 34 and the horn 32 are connected.

The ultrasound vibration generated by the ultrasound transducer 2 is amplified by the horn 32 and transmitted toward the distal end portion 31 of the probe 6. A treatment portion described later configured to treat the living tissue is disposed on the distal end portion 31 of the probe 6.

Two rubber linings 35 are attached at intervals on a circumference surface of the probe main body 34, and the rubber linings 35 are formed in a ring shape by elastic members at several parts of node positions of the vibration in the middle of the axis direction. The rubber linings 35 are configured to prevent contact of the circumference surface of the probe main body 34 and the operation pipe 19 described later.

That is, the probe 6 as a transducer integrated probe is inserted into the operation pipe 19 at assembly of the insertion sheath 8. In this case, the rubber linings 35 prevent contact of the circumference surface of the probe main body 34 and the operation pipe 19.

The ultrasound transducer 2 is electrically connected, through an electrical cable 36, to a power source apparatus main body not shown configured to supply electric current for generating the ultrasound vibration. Power is supplied from the power source apparatus main body to the ultrasound transducer 2 through wiring in the electrical cable 36, and the ultrasound transducer 2 is driven.

As described above, the transducer unit 3 includes: the ultrasound transducer 2 configured to generate ultrasound vibration; the horn 32 configured to amplify the ultrasound vibration generated by the ultrasound transducer 2; and the probe 6 configured to transmit the amplified ultrasound vibration.

(Ultrasound Transducer)

Here, the ultrasound transducer 2 as a stacked ultrasound vibration device of the present invention will be described.

As shown in FIGS. 3 and 4, the ultrasound transducer 2 of the transducer unit 3 includes, in order from the distal end: the horn 32 connected by screwing or the like to the probe main body 34 that is one of vibration transmission members; a stacked transducer 41 in a rectangular shape (quadrangular prism shape) here, consecutively connected behind the horn 32; and a cover body 51 covering the stacked transducer 41 from a proximal end of the horn 32 to the electrical cable 36.

On a proximal end part, the cover body 51 covering the stacked transducer 41 includes a bend preventing portion 52 covering wiring 36a and 36b of the electrical cable 36 electrically connected to two FPCs (flexible printed substrates) 47 and 48 that are energization members. Note that the energization members are not limited to the FPCs 47 and 48, and the energization members may be simple metal lines.

A front side of the stacked transducer 41 is bonded to a front mass 42, which is connected to the horn 32 by screwing or the like and made of a metal block body in a rectangular shape (quadrangular prism shape) here, and a back side is bonded to a back mass 43 made of a metal block body in a rectangular shape (quadrangular prism shape).

Note that the front mass 42 and the back mass 43 need to have a low absorptance of ultrasound vibration and a high strength, and therefore, the front mass 42 and the back mass 43 are formed by duralumin just like the horn 32. The front mass 42 and the back mass 43 may be stainless steel or titanium alloys such as 64Ti (Ti-6Al-4V).

Lengths of the front mass 42 and the back mass 43 are designed such that the ultrasound transducer 2 has a desired resonance frequency.

Furthermore, the stacked transducer 41 may sandwich an insulation member, made of a material with small attenuation for ultrasonic vibration, with the front mass 42 and with the back mass 43 respectively. The insulation member can be, for example, an insulating plate obtained by forming a ceramics material, such as alumina and silicon nitride, into a plate body in a rectangular shape (quadrangular prism shape).

In this way, by providing the insulating member, damage or the like of the stacked transducer 41 caused by a high frequency electrical signal from a treatment instrument is prevented even if the ultrasound medical apparatus 1 shown in FIG. 1 is used together with the treatment instrument, such as a medical high frequency surgical knife, configured to perform a treatment or the like by using a high frequency electrical signal.

Piezoelectric elements formed from a non-lead single crystal material with a high Curie point are used for the stacked transducer 41, and a plurality of, four here, piezoelectric single crystal bodies 61 as piezoelectric single crystal chips that are the piezoelectric elements are stacked and arranged.

Between the four piezoelectric single crystal bodies 61 and the front mass 42 and the back mass 43, positive side bonding metals 62 serving as positive electrode layers and negative side bonding metals 63 serving as negative electrode layers are alternately interposed as bonding metal layers formed from a non-lead solder described later that is a brazing material for bonding the four piezoelectric single crystal bodies 61 and the front mass 42 and the back mass 43.

Note that in the stacked transducer 41, electrical contact portions of the FPCs 47 and 48 are electrically connected by a solder, a conductive paste, or the like to the positive side bonding metals 62 or the negative side bonding metals 63 provided between the piezoelectric single crystal bodies 61 and between the piezoelectric single crystal bodies 61 and the front mass 42 or the back mass 43.

(Manufacturing Method of Ultrasound Transducer)

Next, a manufacturing method of the ultrasound transducer 2 described above will be described in detail.

First, a piezoelectric material with a high Curie temperature (Curie point) and in which piezoelectric characteristics do not deteriorate even at a melting point of a bonding metal is used, and the ultrasound transducer 2 here is created from a piezoelectric single crystal wafer 71 (see FIG. 5) made of lithium niobate (LiNbO3) as a single crystal material.

Note that a wafer with a crystal orientation called a 36 degree rotation Y cut is used for the piezoelectric single crystal wafer 71 to increase an electromechanical coupling coefficient of the piezoelectric element in a thickness direction.

First, as shown in FIGS. 5 and 6, base metals 72 are formed on front and back surfaces of the piezoelectric single crystal wafer 71.

More specifically, the base metals 72 made of, for example, Ti/Ni/Au, Ti/Pt/Au, Cr/Ni/Au, or Cr/Ni/Pd/Au with excellent adhesion and wettability with respect to a non-lead solder are deposited on the front and back surfaces of the piezoelectric single crystal wafer 71 by vapor deposition, sputtering, plating, or the like.

Next, as shown in FIGS. 7 and 8, the piezoelectric single crystal wafer 71 provided with the base metals 72 is cut out and processed into a rectangular shape to form the piezoelectric single crystal body 61 as a piezoelectric body chip.

More specifically, the piezoelectric single crystal wafer 71 is cut out by a dicing blade with a thin thickness along cutting lines (virtual lines) shown in FIG. 7, and a plurality of piezoelectric single crystal bodies 61 as piezoelectric body chips in a rectangular shape as shown in FIG. 8 are fabricated. Such a configuration allows manufacturing a plurality of piezoelectric single crystal bodies 61 inexpensively.

Next, as shown in FIG. 9, a desired number of piezoelectric single crystal bodies 61, the number of piezoelectric signal crystal bodies being four in this embodiment, according to specifications of the ultrasound transducer 2 are stacked. The front mass 42 and the back mass 43 as mass materials are bonded so as to sandwich both ends of the stacked transducer 41 as a stacked body made of the four piezoelectric single crystal bodies 61.

More specifically, first brazing materials 73 that are non-lead solders are provided as first bonding materials between the base metals 72 of the four piezoelectric single crystal bodies 61.

The three first brazing materials 73 interposed between the four piezoelectric single crystal bodies 61 are set to a minimum thickness d1 necessary to bond the piezoelectric single crystal bodies 61 that are similar materials. Note that screen printing or a ribbon format (solder pellet) is used to dispose the first brazing materials 73 on one of the base metals 72 of the piezoelectric single crystal wafers 71.

The front mass 42 and the back mass 43 that are metal blocks are bonded so as to sandwich both ends of the stacked transducer 41 stacked the four piezoelectric single crystal bodies 61 and the three first brazing materials 73.

Here, second brazing materials 76 that are non-lead solders are provided as second bonding materials between the piezoelectric single crystal bodies 61 positioned at both ends and the front mass 42 and the back mass 43.

The second brazing material 76 interposed between the piezoelectric single crystal body 61 and the front mass 42 or the back mass 43 that are dissimilar materials is set to a thickness d2 thicker than the thickness d1 of the first brazing materials 73 as shown in FIG. 10.

Note that screen printing or a ribbon format (solder pellet) is also used to dispose the second brazing materials 76 on the base metals 72 of the piezoelectric single crystal bodies 61 or on one surface of the front mass 42 and the back mass 43, just like the first brazing materials 73.

The four piezoelectric single crystal bodies 61, the front mass 42, and the back mass 43 are heated to a melting temperature of the first brazing materials 73 and the second brazing materials 76 for mutual bonding and are slowly cooled. In this way, the four piezoelectric single crystal bodies 61, the front mass 42, and the back mass 43 are stacked and mutually bonded by the first brazing materials 73 and the second brazing materials 76.

Note that in the heating step of bonding the four piezoelectric single crystal bodies 61, the front mass 42, and the back mass 43, a pressure can be applied for compression in a stacked direction as necessary.

In this way, the four piezoelectric single crystal bodies 61, the front mass 42, and the back mass 43 are stacked, and the ultrasound transducer 2 bonded by the first brazing materials 73 or the second brazing materials 76 is completed.

In the ultrasound transducer 2 manufactured in this way, the base metals 72 deposited on the four piezoelectric single crystal bodies 61 are included, and the positive side bonding metals 62 or the negative side bonding metals 63 are formed by the first brazing materials 73 and the second brazing materials 76.

Note that a screw hole 42*a* with a tap is processed at a center of one end surface of the front mass 42. A screw portion 32*a* integrally formed with the horn 32 is screwed to the screw hole 42*a*, and the horn 32 and the front mass 42 are screwed.

As shown in FIGS. 11 and 12, the two FPCs 47 and 48 that are energization members are mounted on the ultrasound transducer 2.

More specifically, the positive side bonding metals 62 and the negative side bonding metals 63 of the ultrasound transducer 2 are electrically connected to electrical contacts of the FPCs 47 and 48 through electric connectors 49 formed by using a solder, a conductive paste, or the like.

That is, for the electrical connection of the positive side bonding metals 62 and the negative side bonding metals 63 to the FPCs 47 and 48, the electrical contacts of the FPCs 47 and 48 come into contact with outer surfaces of the positive side bonding metals 62 and the negative side bonding metals 63 through the electric connectors 49, and the FPCs 47 and 48 are fixed to the stacked transducer 41.

In this way, the electrical connection of the positive side bonding metals 62 and the negative side bonding metals 63 to the FPCs 47 and 48 is established. The wiring 36a and 36b (see FIGS. 3 and 4) of the electrical cable 36 are connected to the FPCs 47 and 48.

Note that although FIGS. 10 to 12 illustrate a state that the horn 32 and the front mass 42 are screwed, the horn 32 and the front mass 42 can be bonded by screwing before or after the installation of the FPCs 47 and 48 on the ultrasound transducer 2.

According to the configuration, the wiring 36a of the electrical cable 36, the FPC 47, the electric connectors 49, and the positive electrode side metals 62 are electrically connected on a positive electrode side. The wiring 36b of the electrical cable 36, the FPC 48, the electric connectors 49, and the negative electrode metals 63 are electrically connected on a negative electrode side. Based on the electrical connections, the drive signal is applied to the four piezoelectric single crystal bodies 61 through the positive side bonding metals 62 and returned from the negative side bonding metals 63.

Note that exposed surface parts of the positive side bonding metals 62, the negative side bonding metals 63, and the electric connector 49 may be covered by an insulating body, such as a resin, to prevent generation of an unnecessary electrical connection that causes a failure, or the FPCs 47 and 48 may be fixed by an adhesive to the positive side bonding metals 62 and the negative side bonding metals 63 in order to reinforce the mechanical fixation of the FPCs 47 and 48. Furthermore, the FPCs 47 and 48 may be fixed by an adhesive on surfaces of side portions of the four piezoelectric single crystal bodies 61.

According to the manufacturing process of the ultrasound transducer 2 described above, the front mass 42, the four piezoelectric single crystal bodies 61, and the back mass 43 in order from the distal end are bonded and integrated by the first brazing materials 73 and the second brazing materials 76 serving as bonding metal layers and serving as the positive side bonding metals 62 and the negative side bonding metals 63. The drive signal is applied from the FPCs 47 and 48 provided on the side face of the stacked body to the positive side bonding metals 62 through the electric connectors 49 and is returned by the negative side bonding metals 63 to thereby generate ultrasound vibration of the entire ultrasound transducer 2.

By the way, the parts for bonding the piezoelectric single crystal bodies 61 of the stacked transducer 41 in the ultrasound transducer 2 are similar materials, lithium niobate (LiNbO3) here, and therefore thermal stress generated in the four piezoelectric single crystal bodies 61 due to temperature changes during the bonding and during the drive is small.

On the other hand, parts for bonding the piezoelectric single crystal bodies 61 to the front mass 42 and the back mass 43 are bonding of dissimilar materials. Therefore, a difference between two different materials, a thermal expansion coefficient (8 to $15 \times 10^{-6}$ [1/° C.]) of lithium niobate (LiNbO3) and a thermal expansion coefficient ($24 \times 10^{-6}$ [1/° C.]) of duralumin here, generates thermal stress in the two piezoelectric single crystal bodies 61 at both ends bonded to the front mass 42 or the back mass 43, and the thermal stress is greater than that at the similar material bonding portion due to temperature changes during bonding and during drive.

Therefore, large thermal stress is generated in the two piezoelectric single crystal bodies 61 at both ends bonded to the front mass 42 or the back mass 43. Stress is generated inside along with an increase in internal force, and a crack is generated.

Furthermore, the first brazing materials 73 and the second brazing materials 76 forming the positive side bonding metals 62 or the negative side bonding metals 63 are soft materials with Young's moduli (elastic constants) smaller than those of the piezoelectric single crystal bodies 61, the front mass 42, and the back mass 43.

Therefore, although the first brazing materials 73 or the second brazing materials 76 operates to absorb the thermal stress generated in the piezoelectric single crystal bodies 61, absorptance of the ultrasound generated in the ultrasound transducer 2 is also large.

Therefore, if the thicknesses of the first brazing materials 73 and the second brazing materials 76 are too thick, characteristics of the ultrasound transducer 2 as a Langevin transducer are deteriorated.

To prevent this, in the ultrasound transducer 2 of the present embodiment, the thickness of the first brazing materials 73 as similar material bonding portions for the bonding between the four piezoelectric single crystal bodies 61 as similar materials is set to the minimum thickness d1 necessary for the bonding of the four piezoelectric single crystal bodies 61, and the thickness d2 of the second brazing materials 76 as dissimilar material bonding portions with relatively large thermal stress is thicker than the thickness d1 of the first brazing materials 73 (d1<d2). As a result, the thermal stress during the heating step and during the drive is unlikely to be transmitted to the two piezoelectric single crystal bodies 61 at both ends.

In other words, the Young's modulus (elastic constant) of the second brazing materials 76 is smaller than the Young's moduli of the piezoelectric single crystal bodies 61, the front mass 42, and the back mass 43, and the second brazing materials 76 are soft. Therefore, the second brazing materials 76 are thick in the ultrasound transducer 2, and the second brazing materials 76 function as stress buffer layers for bonding the piezoelectric single crystal bodies 61 to the front mass 42 or the back mass 43 that are dissimilar material bonding portions.

Although it is preferable that the stress buffer layers have a large thickness, a loss of ultrasound generated in the ultrasound transducer 2 by the stress buffer layer is larger than that by the piezoelectric single crystal bodies 61 made of duralumin and lithium niobate (LiNbO3) used for the front mass 42 and the back mass 43.

Therefore, it is desirable that volumes of the first brazing materials 73 and the second brazing materials 76 be as small as possible. That is, when the volumes of the first brazing materials 73 and the second brazing materials 76 are small, the loss of the generated ultrasound is small in the entire ultrasound transducer 2.

Therefore, the first brazing materials 73 with the minimum thickness d1 necessary for the bonding portions between the four piezoelectric single crystal bodies 61 with almost no thermal stress are used in the ultrasound transducer 2 of the present embodiment to prevent the reduction of performance (reduction of Q value), and the second brazing materials 76 with the thickness d2 thicker than that of the first brazing materials 73 are used for the bonding portions of the two piezoelectric single crystal bodies 61 provided at both ends with notable thermal stress due to the difference in the thermal expansion coefficients and the front mass 42 or the back mass 43. In this way, the thermal stress is reduced, and a crack of the two piezoelectric single crystal bodies 61 provided on the dissimilar material bonding portions is prevented.

As a result, the ultrasound transducer 2 can prevent the degradation of performance of the entire ultrasound transducer 2 while preventing a crack of the two piezoelectric single crystal bodies 61 provided at both ends bonded to the front mass 42 or the back mass 43.

Note that to reduce the thermal stress generated in the piezoelectric single crystal bodies 61, it is desirable to use bonding metals with thermal expansion coefficients between the thermal expansion coefficient (8 to $15\times10^{-6}$ [1/° C.]) of the piezoelectric single crystal bodies 61 and the thermal expansion coefficient ($24\times10^{-6}$ [1/° C.]) of the front mass 42 and the back mass 43 for the first brazing materials 73 and the second brazing materials 76.

A Sn—Ag—Cu-based solder with a thermal expansion coefficient between the thermal expansion coefficient of the piezoelectric single crystal bodies 61 made of lithium niobate (LiNbO3) and the thermal expansion coefficient of the front mass 42 and the back mass 43 made of duralumin is used for the first brazing materials 73 and the second brazing materials 76, for example.

The thermal expansion coefficient of the Sn—Ag—Cu-based solder used for the first brazing materials 73 and the second brazing materials 76 is $21\times10^{-6}$ [1/° C.] which is greater than the thermal expansion coefficient (8 to $15\times10^{-6}$ [1/° C.]) of lithium niobate (LiNbO3) and smaller than the thermal expansion coefficient ($24\times10^{-6}$ [1/° C.]) of duralumin.

As a result, the second brazing materials 76 made of the Sn—Ag—Cu-based solder that is a bonding material of the two piezoelectric single crystal bodies 61 provided at both ends and the front mass 42 and the back mass 43 particularly play a role of absorbing the difference between the thermal expansion coefficient of the two piezoelectric single crystal bodies 61 provided at both ends and the thermal expansion coefficient of the front mass 42 and the back mass 43. The stress on the piezoelectric single crystal bodies 61 is reduced, and generation of a crack inside the piezoelectric single crystal bodies 61 is prevented.

Note that it is only necessary that the thermal expansion coefficient of the second brazing materials 76 be between the thermal expansion coefficients of lithium niobate (LiNbO3) and duralumin, and other than the Su-Ag—Cu-based solder, a Sn-based solder, a Sn—Ag-based solder, or a Sn—Cu-based solder may be used, for example.

Furthermore, the thermal stress generated in the piezoelectric single crystal bodies 61 due to the difference between the thermal expansion coefficient of the piezoelectric single crystal bodies 61 and the thermal expansion coefficient of the front mass 42 and the back mass 43 is generated as indicated by a curve as shown in FIG. 13 according to the thickness of the second brazing materials 76.

Note that P1 on the curve of FIG. 13 denotes a point in which the piezoelectric single crystal bodies 61 are cracked due to thermal stress σ1 generated by the difference between the thermal expansion coefficient of the piezoelectric single crystal bodies 61 and the thermal expansion coefficient of the front mass 42 and the back mass 43.

Here, based on P1, the thickness d2 of the second brazing materials 76 as bonding metals is set between a thickness d2min indicated by P2 based on a predetermined safety factor (for example, half the thermal stress σ1) that does not cause a crack even if thermal stress σ2 is generated in the piezoelectric single crystal bodies 61 and a thickness d2max indicated by P3 with which there is almost no change in thermal stress σ3 generated in the piezoelectric single crystal bodies 61 even if the thickness of the brazing materials 76 is changed.

Note that as shown in FIG. 13, even if the thickness d2 of the second brazing materials 76 exceeds the thickness d2max, the thermal stress σ3 generated in the piezoelectric single crystal bodies 61 due to the difference between the thermal expansion coefficient of the piezoelectric single crystal bodies 61 and the thermal expansion coefficient of the front mass 42 and the back mass 43 does not change. Therefore, if the thickness d2 is thicker than the thickness d2max, the performance of the ultrasound transducer 2 is further reduced.

Therefore, it is most preferable to set the thickness d2 of the second brazing materials 76 to the thickness d2max if the loss of ultrasound generated in the ultrasound transducer 2 is within a permissible range of specifications. That is, an upper limit of the thickness d2 of the second brazing materials 76 is d2max that is a smallest thickness with which the thermal stress σ3 generated in the piezoelectric single crystal bodies 61 does not change.

Furthermore, to make the thickness d2 of the second brazing materials 76 thicker than the thickness d1 of the first brazing materials 73, the thickness can be set in screen printing, or a thick solder pellet can be prepared. Therefore, the ultrasound transducer 2 can be realized inexpensively without an extra step or without a change in the process or the like.

Note that when the ribbon format (solder pellet) is used for the first brazing materials 73 and the second brazing materials 76, a plurality of, two here, first brazing materials 73 can be placed on each other to form the second brazing material 76 as shown for example in FIG. 14. In this way, materials with different thickness do not have to be prepared. That is, the thickness of the second brazing materials 76 can be set to the thickness d2 that is an integral multiple of the first brazing materials 73, and therefore the cost can be further reduced.

Although the ultrasound transducer 2 has a rectangular block shape that can be most inexpensively manufactured in the example described above, the shape is not limited to this. For example, the shapes of the members may be columnar shapes.

As described above, the ultrasound transducer 2 that is a stacked ultrasound vibration device of the present embodiment and the ultrasound medical apparatus 1 including the ultrasound transducer 2 can be inexpensively manufactured, and damage or the like of piezoelectric bodies due to stress caused by a difference between a thermal expansion coefficient of metal blocks as mass materials and a thermal expansion coefficient of the piezoelectric bodies can be prevented.

The invention described in the embodiment is not limited to the embodiment and modifications, and various modifications can also be carried out in an execution phase without departing from the scope of the invention. Furthermore, the embodiment includes inventions of various phases, and various inventions can be extracted based on appropriate combinations of a plurality of disclosed constituent elements.

For example, when the problem can be solved and the advantageous effects can be obtained even if some of the constituent elements illustrated in the embodiment are removed, the configuration after the removal of the constituent elements can be extracted as an invention.

What is claimed is:

1. A stacked ultrasound vibration device comprising:
a piezoelectric body comprising:
a plurality of piezoelectric layers; and
first metal bonding layers each having a first thickness for bonding the plurality of piezoelectric layers together;
a mass material; and
a second metal bonding layer being a different material from the first metal bonding layers, the second metal bonding layer having a second thickness thicker than the first thickness and the second metal bonding layer bonding the mass material to the piezoelectric body,
wherein the first metal bonding layers and the second metal bonding layer comprise brazing materials whose elastic constants are smaller than elastic constants of the plurality of piezoelectric layers and the mass material.

2. The stacked ultrasound vibration device according to claim 1, wherein the plurality of piezoelectric layers are piezoelectric single crystal materials.

3. The stacked ultrasound vibration device according to claim 1, wherein the first metal bonding layers and the second metal bonding layer serve as electrode layers.

4. The stacked ultrasound vibration device according to claim 1, wherein first and second thermal expansion coefficients of the first metal bonding layers and the second metal bonding layer, respectively, are in a range between a thermal expansion coefficient of the plurality of piezoelectric layers and a thermal expansion coefficient of the mass material.

5. The stacked ultrasound vibration device according to claim 1, wherein:
a solder pellet with the first thickness is used for each of the first metal bonding layers, and
the second thickness is set to an integral multiple of the first thickness.

6. The stacked ultrasound vibration device according to claim 1, wherein an upper limit of the second thickness is set to a smallest thickness with which thermal stress generated in the plurality of piezoelectric layers due to a difference between a thermal expansion coefficient of the plurality of piezoelectric layers and a thermal expansion coefficient of the mass material does not change.

7. An ultrasound medical apparatus comprising:
the stacked ultrasound vibration device according to claim 1; and
a probe configured to receive ultrasound vibration generated by the stacked ultrasound vibration device to treat living tissue.

8. The stacked ultrasound vibration device according to claim 1, wherein:
the mass material comprises first and second mass materials and the second metal bonding layer comprises two second metal bonding layers;
the first mass material being bonded to a first end of the piezoelectric body with one of the two second metal bonding layers; and
the second mass material being bonded to a second end of the piezoelectric body with an other of the two second metal bonding layers.

9. The stacked ultrasound vibration device according to claim 8, wherein first and second thermal expansion coefficients of the first metal bonding layers and the second metal bonding layer, respectively, are in a range between a thermal expansion coefficient of the plurality of piezoelectric layers and a thermal expansion coefficient of the first and second mass materials.

10. The stacked ultrasound vibration device according to claim 8, wherein an upper limit of the second thickness is set to a smallest thickness with which thermal stress generated in the plurality of piezoelectric layers due to a difference between a thermal expansion coefficient of the plurality of piezoelectric layers and a thermal expansion coefficient of the first and second mass materials does not change.

* * * * *